United States Patent [19]

Muto et al.

[11] Patent Number: 4,501,748
[45] Date of Patent: Feb. 26, 1985

[54] 1,4-DIHYDROPYRIDINE DERIVATIVES

[75] Inventors: Kenji Muto; Akira Karasawa, both of Shizuoka; Tokuyuki Kuroda, Susono; Nobuhiro Nakamizo, Machida, all of Japan

[73] Assignee: Kyowa Hakko Kogyo Co., Ltd., Tokyo, Japan

[21] Appl. No.: 542,181

[22] Filed: Oct. 14, 1983

[30] Foreign Application Priority Data

Jun. 3, 1983 [JP]  Japan .................................. 58-98899

[51] Int. Cl.³ ................. A61K 31/445; C07D 211/90; C07D 401/12
[52] U.S. Cl. ..................................... 514/318; 546/194
[58] Field of Search ......................... 546/194; 424/267

[56] References Cited

U.S. PATENT DOCUMENTS 4,448,964  5/1984  Muto et al. .......................... 546/194

FOREIGN PATENT DOCUMENTS 63365  10/1982  European Pat. Off. ............ 424/267

Primary Examiner—Robert T. Bond
Attorney, Agent, or Firm—Antonelli, Terry & Wands

[57] ABSTRACT

An optical isomer having an optical rotation degree of (+) from among (±)-α-2,6-dimethyl-4-(3-nitrophenyl)-1,4-dihydropyridine-3,5-dicarboxylic acid-3-(1-benzyl-3-piperidyl) ester-5-methyl ester, the hydrochloride of which has melting points ranging from 196° to 202° C.; or a salt thereof is described as being suitable for use in a pharmaceutical composition having hypotensive activity.

4 Claims, No Drawings

1,4-DIHYDROPYRIDINE DERIVATIVES

The present invention relates to 1,4-dihydropyridine derivatives. More particularly, the present invention relates to an optical isomer having an optical rotation degree of (+) from among (±)-2,6-dimethyl-4-(3-nitrophenyl)-1,4-dihydropyridine-3,5-dicarboxylic acid-3-(1-benzyl-3-piperidyl)ester-5-methyl ester, the hydrochloride of which has melting points of 196° to 202° C.; or a salt thereof.

The present inventors with another have already filed a Japanese Patent Application directed to (±)-2,6-dimethyl-4-(3-nitrophenyl)-1,4-dihydropyridine-3,5-dicarboxylic acid-3-(1-benzyl-3-piperidyl)ester-5-methyl ester [(±)-α-form], the hydrochloride of which has melting points of 196° to 202° C. (Japanese Patent Application No. 180616/82).

As a result of various subsequent studies, it has been found that among the (±)-α-form, of these 1,4-dihydropyridine derivatives, particularly the (+)-α-form has an excellent hypotensive effect.

One example of the processes for producing the present compounds is shown below.

Process:

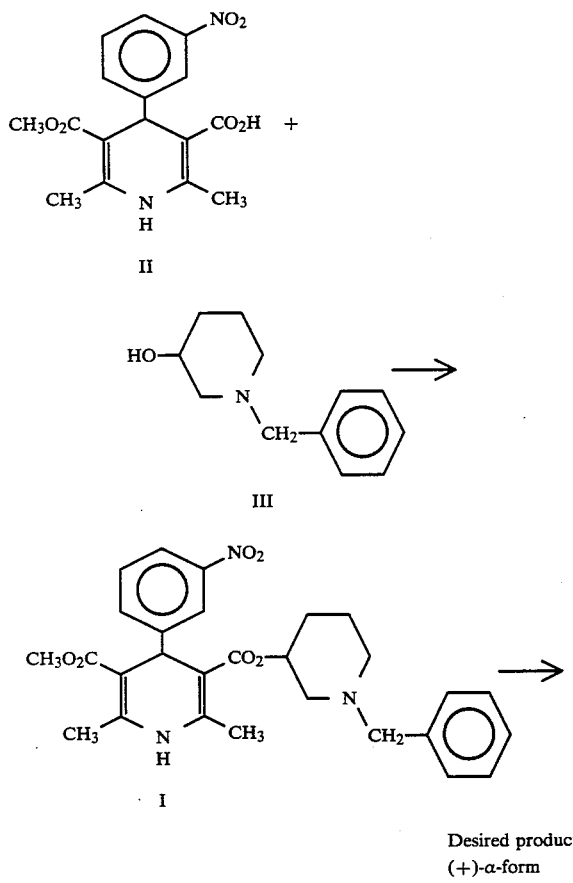

Desired product
(+)-α-form

An optically active form having an optical rotation degree of (−) or a racemate of the compound represented by the formula II (hereinafter referred to as Compound II; compounds of formulae I and III are similarly referred to) is suitable as a starting material, and similarly an optically active form having an optical rotation degree of (+) or a racemate of Compound III is preferred as a starting material.

Esterification reaction between Compounds II and III is carried out in a conventional manner; e.g., (a) a process which comprises converting Compound II into the acid halide using a halogenating reagent and then reacting the acid halide with Compound III;

(b) a process which comprises reacting Compound II with Compound III in the presence of the condensing agent such as N,N'-dicyclohexylcarbodiimide; and the process (a) using an inexpensive halogenating reagent (for example, thionyl chloride, phosphorus trichloride, phosphorus pentachloride, phosphorus oxychloride and phosphorus tribromide) is particularly advantageous.

The process (a) is explained in further detail.

The process in which the halogenating reagent is thionyl chloride, is illustrated by the following equations:

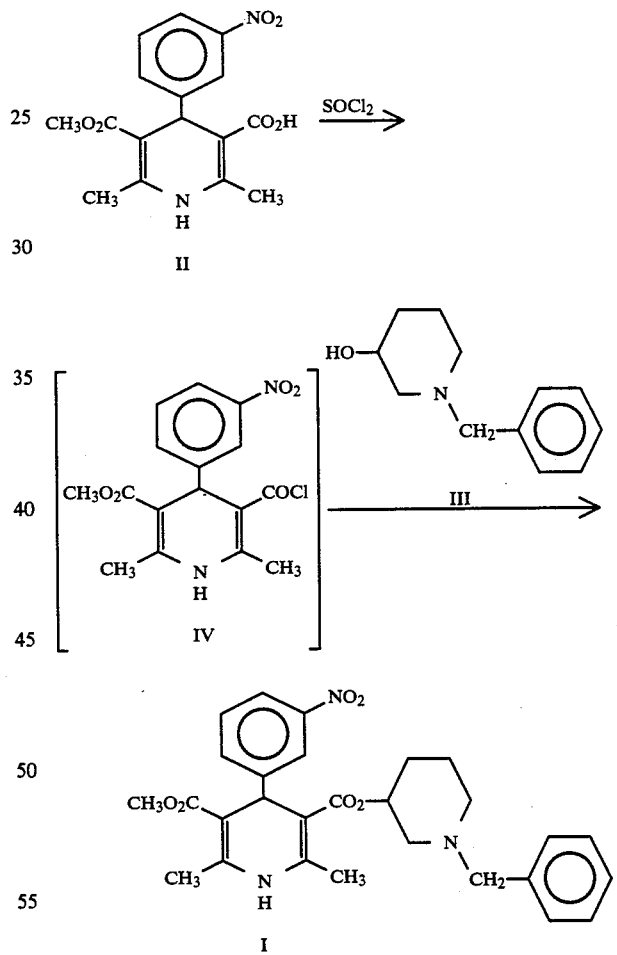

The reaction is carried out in the presence or absence of halogenated hydrocarbons such as dichloromethane, chloroform, carbon tetrachloride and chlorobenzene; aromatic hydrocarbons such as benzene and toluene; ethers such as tetrahydrofuran and dioxane; aprotic polar solvents such as acetonitrile, N,N-dimethylformamide and hexamethylphosphoric triamide; amines such as pyridine and triethyl amine. The reaction is preferably carried out using thionyl chloride as the halogenating reagent in the presence of N,N-dimethylformamide or hexamethylphosphoric triamide as a reaction solvent alone or using the aforesaid solvents in combination.

The molar ratio of Compound II to thionyl chloride ranges from 1.0:0.8–1.0:2.0, preferably 1.0:0.9–1.0:1.2.

The molar ratio of thionyl chloride to N,N-dimethylformamide or hexamethylphosphoric triamide is 1:1–1:100, preferably 1:5–1:50.

The reaction is carried out at temperatures of −70° C. to 100° C., preferably −20° C. to 50° C.

Then, the resulting Compound IV (which may not be isolated) is reacted with Compound III to thereby obtain Compound I.

As the solvent, the same solvent as employed for preparation of Compound IV from Compound II is employed.

The molar ratio of Compound II to Compound III is in the range of 1.0:0.8–1.0:2.0, preferably 1.0:0.9–1.0:1.2 and the reaction temperature is −70° C. to 100° C., preferably −20° C. to 50° C.

Compound II and Compound III which are employed as starting materials are known compounds. Furthermore, optically active Compound III can also be readily produced from known optically active Compound V by the following reaction.

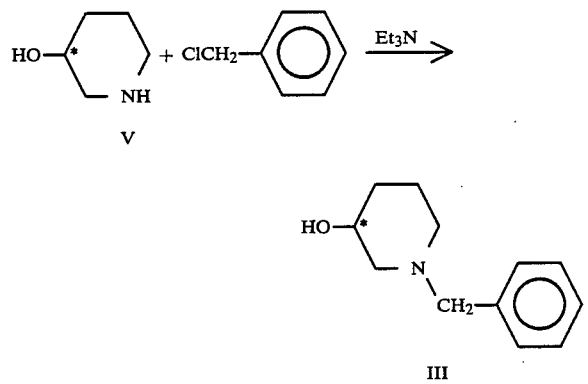

(* represents an asymmetric carbon.)

Compound II: T. Shibanuma et al., Chem. Pharm. Bull., 28, 2809 (1980)

Compound V: H. Sievertsson et al., J. Med. Chem., 15, 1085 (1972)

The desired product, (+)-α-form may be isolated from the resulting reaction mixture as follows.

In case that Compound II and Compound III are both optically active substances (Compound II is (−) form and Compound (III) is (+) form), the product is principally only (+)-α-form; therefore, the desired product can be isolated by procedures such as extraction and concentration and, if necessary, column chromatography may also be carried out.

In case that either Compound II or Compound III is a racemate, the desired product can be isolated by column chromatography in addition to extraction, concentration, etc., since (+)-β-form or (−)-β-form is contained in the reaction mixture, in addition to the desired (+)-α-form. Furthermore, if deemed necessary, the isolated free product is reacted with inorganic acids such as hydrochloric acid, hydrobromic acid, phosphoric acid and sulfuric acid, or organic acid such as formic acid, acetic acid, fumaric acid, maleic acid, malic acid and tartaric acid to prepare pharmaceutically acceptable acid addition salts thereof.

The acute toxicity and hypotensive effect of the present compound are described below.

ACUTE TOXICITY

Drugs were compulsorily orally administered to mice (ddY type, body weight of 20 to 24 g, male) and the survival rate 72 hours after the administration was studied. A suspension of each of the drugs in water having added a small quantity of Tween 80 thereto was orally given at the dose of 0.1 ml/10 g mouse body weight, using a gastric tube.

| | Acute Toxicity $LD_{50}$ (mg/kg · po) |
|---|---|
| (+)-α-form | 95 |
| (−)-α-form | 918 |
| (±)-α-form | 218 |

HYPOTENSIVE EFFECT (1.) Intravenous Administration to SHR (no anesthesia)

Spontaneously hypertensive rat (SHR) (Okamoto strain, aging 20 to 30 weeks, male) were anesthetized with sodium thiopental (50 mg/kg, ip). A cannula for measuring blood pressure was inserted into the descending aorta from the right femoral artery and a cannula for intravenous administration was inserted into the left carotid vein, and these cannulas were fixed on the back carotid, respectively. Change in blood pressure by intravenous administration of each of drugs were measured next day without any anesthesia. As the drugs, a solution of each of the drugs in polyethylene glycol 400 was intravenously administered at the dose of 0.1 ml/100 g body weight of the rat.

The results are shown in Table 1.

TABLE 1

| | Dose Administered (μg/kg i.v.) | Number of Animals | Maximum Decrease in Mean Blood Pressure (mmHg) |
|---|---|---|---|
| (+)-α-form | 1 | 5 | 42.2 ± 11.5 |
| (+)-α-form | 10 | 5 | 67.4 ± 4.7 |
| (−)-α-form | 10 | 5 | 23.4 ± 7.9 |
| (−)-α-form | 100 | 5 | 27.3 ± 6.1 |
| (±)-α-form | 1 | 5 | 23.1 ± 6.4 |
| (±)-α-form | 10 | 5 | 45.6 ± 6.5 |

(2) Oral Administration to SHR (no anesthesia)

Change in systolic blood pressure when drugs were orally administered to spontaneously hypertensive rat (SHR) (Okamoto Strain, aging 15 to 26 weeks, male) was measured by the plethysmographic tail method (Ueda Seisakusho, USM-105R).

Drugs were compulsorily orally administered at the dose of 0.5 ml/100 g body weight of the rat in the form of a suspension in 0.3% carboxymethyl cellulose, using a gastric tube.

The results are shown in Table 2.

TABLE 2

| Drug | Dose Administered (mg/kg p.o.) | Number of Animals | Maximum Decrease in Systolic Blood Pressure (mmHg) |
|---|---|---|---|
| (+)-α-form | 1 | 8 | 56.3 ± 13.0 |
| (−)-α-form | 3 | 4 | 22.5 ± 9.6 |
| (−)-α-form | 10 | 4 | 30.0 ± 5.3 |
| (±)-α-form | 1 | 8 | 35.6 ± 6.3 |

The compounds of the present invention, in consideration of their pharmaceutical effect, may be employed in various pharmaceutical forms for the intended administration, and in particular, they are preferably employed in oral forms such as tablets and powders.

In the case of tablets, the compound of the present invention may be contained in an amount of 1–30% (W/W) per tablet. As other components (carriers), commonly employed excipients, disintegrators, lubricants, binders, coating agents, etc., may be employed.

For example, there may be mentioned excipients such as glucose and lactose; disintegrators such as starch and calcium carboxymethyl cellulose; lubricants such as magnesium stearate and talc; binders such as simple syrup, polyvinyl alcohol, gelatin and hydroxypropyl cellulose; and coating agents such as dispersants (e.g, methyl cellulose and ethyl cellulose); and plasticisers (e.g., glycerin and polyethylene glycol). Microcrystalline cellulose partakes of the properties of disintegrators of binders and of excipients.

In the case of powders, the compound of the present invention may be contained in an amount of 1–20% (W/W). As the carriers, excipients such as glucose and lactose; binders such as hydroxypropyl cellulose and the like may be employed. The $LD_{50}$ of the compound of the present invention [(+)-α-form] in the oral administration in male rats is 95 mg/kg. The dose is preferably in the range of 1–50 mg per day for a human adult weight ca. 60 kg.

The present invention is more particularly described by the following examples and reference examples.

EXAMPLE 1

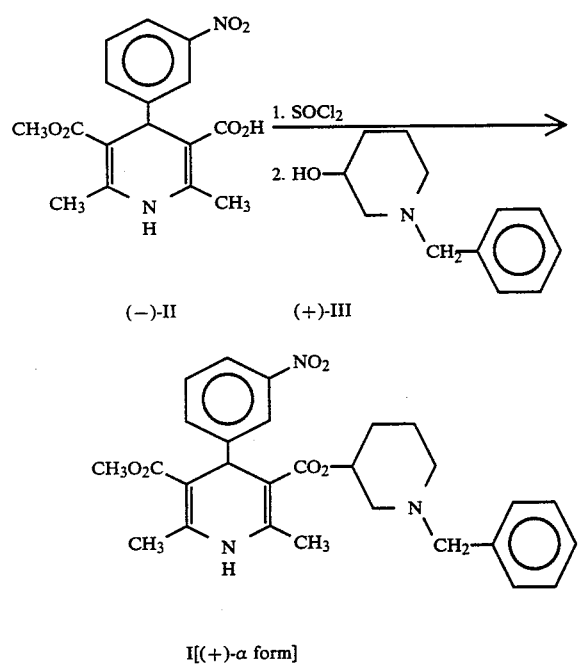

In 17 ml of a mixed solvent of dichloromethane and N,N-dimethylformamide (4:1 v/v), 2.50 g of (−)-2,6-dimethyl-4-(3-nitrophenyl)-1,4-dihydropyridine-3,5-dicarboxylic acid monomethyl ester was suspended and to the suspension was added 0.57 ml of thionyl chloride under ice cooling. After stirring under ice cooling for one hour, 1.51 g of (+)-1-benzyl-3-hydroxypiperidine obtained in Reference Example 1 was added to the mixture and stirring was further continued under ice cooling for 2 hours. The reaction mixture was diluted with 25 ml of dichloromethane, and washed with 30 ml of water and then with 30 ml of brine. The dichloromethane layer was dried over anhydrous sodium sulfate and concentrated under reduced pressure. The concentrate was subjected to silica gel column chromatography (eluent, chloroform: ethyl acetate=1:1 v/v) and fractions containing the desired product were concentrated. To the concentrate were added 30 ml of chloroform and 10 ml of 4N hydrochloric acid. After vigorously stirring the mixture, the chloroform layer was washed twice with 20 ml of water, then dried over anhydrous sodium sulfate, and concentrated to dryness to obtain 4.20 g of amorphous powders. The powders were dissolved in 15 ml of acetone and the solution was added to 200 ml of ether. The mixture was stirred to observe precipitates. The precipitates were filtered and dried to obtain 2.72 g of (+)-α-2,6-dimethyl-4-(3-nitrophenyl)-1,4-dihydropyridine-3,5-dicarboxylic acid-3-(1-benzyl-3-piperidyl)ester-5-methyl ester hydrochloride.

$[\alpha]_D^{21}+113.6$ (c=0.50, acetone).

IR (KBr, cm$^{-1}$): 1680, 1525, 1350.

NMR (DMSO-d$_6$, δ): 1.3–2.2(4H, broad), 2.33 (6H, s), 2.7–3.4(4H, broad), 3.57(3H, s), 4.40(2H, s), 4.98(1H, s), 5.20(1H, broad), 7.3–8.2(9H, m), 9.47(1H, broad).

EXAMPLE 2

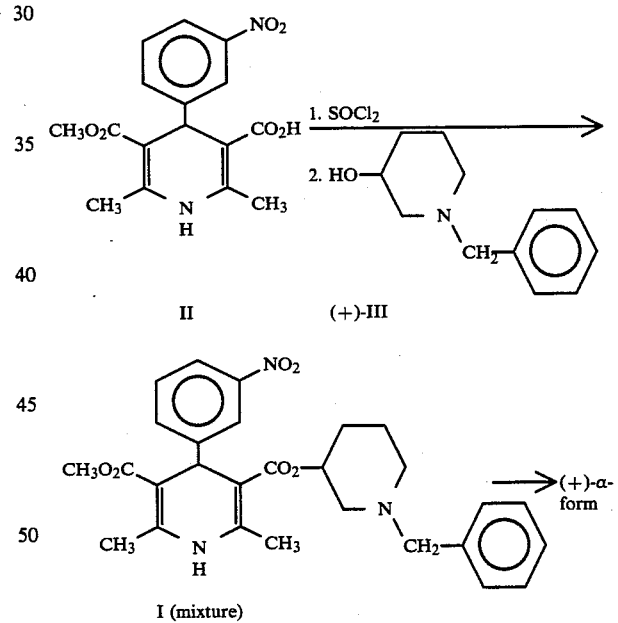

In 17 ml of a mixed solvent of dichloromethane and N,N-dimethylformamide (4:1 v/v), 2.50 g of 2,6-dimethyl-4-(3-nitrophenyl)-1,4-dihydropyridine-3,5-dicarboxylic acid monomethyl ester was suspended and to the suspension was added 0.57 ml of thionyl chloride under ice cooling. After stirring under ice cooling for one hour, 1.51 g of (30 )-1-benzyl-3-hydroxypiperidine obtained in Reference Example 1 was added to the mixture and stirring was further continued under ice cooling for 2 hours and 40 minutes. The reaction mixture was diluted with 50 ml of dichloromethane and washed with 50 ml of 5% sodium hydrogen carbonate, 50 ml of water and then 50 ml of brine. The dichloromethane layer was dried over anhydrous sodium sulfate, and concentrated under reduced pressure. The concentrate was subjected to silica gel column chromatography (eluent, chloroform:ethyl acetate:triethyl amine=50:50:1 v/v) to separate (+)-α-form from (+)-β-form. Fraction containing the desired (+)-α-form was concentrated and dissolved in 20 ml of acetone. To the solution was added 5 ml of 4N hydrochloric acid. After stirring the mixture, acetone was removed by distillation under reduced pressure. To the residue remained after the concentration was added 20 ml of chloroform. The chloroform layer was washed twice with 20 ml of water, then dried over anhydrous sodium sulfate, and concentrated to dryness to obtain 1.02 g of amorphous powders of (+)-α-2,6-dimethyl-4-(3-nitrophenyl)-1,4-dihydropyridine-3,5-dicarboxylic acid-3-(1-benzyl-3-piperidyl)ester-5-methyl ester hydrochloride.

$[\alpha]_D^{21} + 110.7$ (c=0.50, acetone).

IR and NMR spectra were identical with those of the compound obtained in Example 1.

REFERENCE EXAMPLE 1

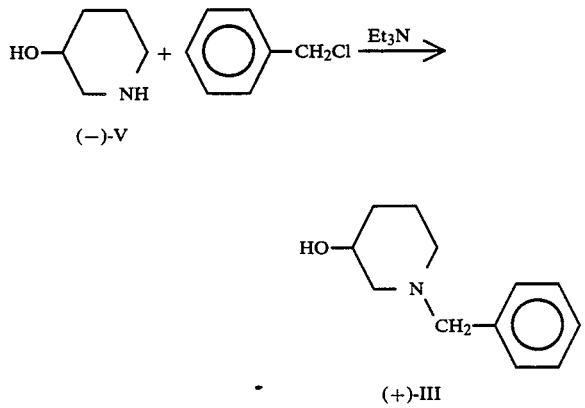

After stirring 8.53 g of (−)-3-hydroxypiperidine, 7.72 g of benzyl chloride and 6.17 g of triethyl amine in 70 ml of toluene for 5 hours under reflux, the mixture was filtered and the filtrate was concentrated under reduced pressure. The residue was distilled under reduced pressure to obtain 5.49 g of a distillate having a boiling point of 103.8° C./0.5 mmHg.

$[\alpha]_D^{23} + 11.9$ (c=2.14, methanol).

REFERENCE EXAMPLE 2

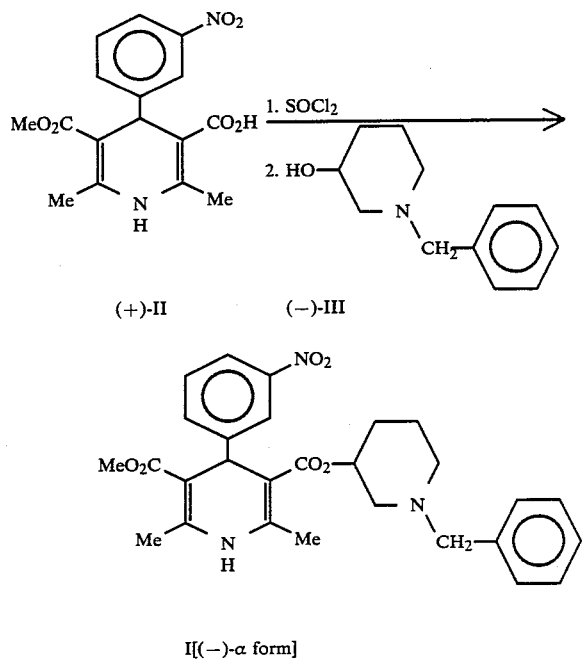

In a similar manner to Example 1, 3.16 g of amorphous powders of (−)-α-2,6-dimethyl-4-(3-nitrophenyl)-1,4-dihydropyridine-3,5-dicarboxylic acid-3-(1-benzyl-3-piperidyl)ester-5-methyl ester hydrochloride were obtained except that 2.50 g of (+)-2,6-dimethyl-4-(3-nitrophenyl)-1,4-dihydropyridine-3,5-dicarboxylic acid monomethyl ester and 1.51 g of (−)-1-benzyl-3-hydroxypiperidine were employed in place of (−)-2,6-dimethyl-4-(3-nitrophenyl)-1,4-dihydropyridine-3,5-dicarboxylic acid monomethyl ester and (+)-1-benzyl-3-hydroxypiperidine used in Example 1, respectively.

$[\alpha]_D^{22} - 110.2$ (c=0.24, acetone).

What is claimed is:

1. An optical isomer having an optical rotation degree of (+) from among (±)-α-2,6-dimethyl-4-(3-nitrophenyl)1,4-dihydropyridine-3,5-dicarboxylic acid-3-(1-benzyl-3-piperidyl) ester-5-methyl ester, the hydrochloride of which has melting points ranging from 196° to 202° C.; or a salt thereof.

2. An optical isomer according to claim 1; namely, (+)-α-2,6-dimethyl-4-(3-nitrophenyl)-1,4-dihydropyridine-3,5-dicarboxylic acid-3-(1-benzyl-3-piperidyl)ester-5-methyl ester.

3. An optical isomer according to claim 1; namely, (+)-α-2,6-dimethyl-4-(3-nitrophenyl)-1,4-dihydropyridine-3,5-dicarboxylic acid-3-(1-benzyl-3-piperidyl)ester-5-methyl ester hydrochloride.

4. A pharmaceutical composition which has hypotensive effects and which comprises an effective amount of an optical isomer according to claim 1, as an active ingredient and a pharmaceutical carrier.

* * * * *